United States Patent
Cogswell

(10) Patent No.: US 7,594,898 B2
(45) Date of Patent: Sep. 29, 2009

(54) SLEEP-AIDING DEVICE

(76) Inventor: Richard Cogswell, Jameson La., Spencer, MA (US) 01562

( * ) Notice: Subject to any disclaimer, the term of this patent is extended or adjusted under 35 U.S.C. 154(b) by 971 days.

(21) Appl. No.: 10/800,466

(22) Filed: Mar. 15, 2004

(65) Prior Publication Data

US 2004/0181852 A1    Sep. 23, 2004

Related U.S. Application Data

(60) Provisional application No. 60/455,484, filed on Mar. 18, 2003.

(51) Int. Cl.
*A61F 5/00* (2006.01)
*A61F 13/00* (2006.01)

(52) U.S. Cl. .............. 602/36; 602/23; 602/32; 602/60; 602/62

(58) Field of Classification Search ............. 602/32–36, 602/23, 60, 62
See application file for complete search history.

(56) References Cited

U.S. PATENT DOCUMENTS

| 504,598 | A | * | 9/1893 | Leyda .................. 601/45 |
| 3,805,773 | A | | 4/1974 | Sichau |
| 5,643,184 | A | * | 7/1997 | Toso .................. 602/19 |
| 5,882,321 | A | | 3/1999 | Fisk |
| 5,921,945 | A | | 7/1999 | Gray |

* cited by examiner

*Primary Examiner*—Kim M Lewis
(74) *Attorney, Agent, or Firm*—Fish & Richardson P.C.

(57) ABSTRACT

A sleep-aiding device for restricting stretching of a wearer's legs to full extension to reduce leg muscle cramping during sleep includes an adjustable belt worn about a wearer's waist during sleep, with leg members extending between the belt at the wearer's waist and attachment at lower portions of the wearer's legs, generally below the wearer's knees, e.g. in a preferred embodiment by engagement of the wearer's feet through end loops positioned midway between the toes and ankle. The leg members have predetermined lengths between the belt and attachment at the lower portions of the wearer's legs that are adjustably selected to restrict stretching of the wearer's legs to full extension during sleep.

5 Claims, 4 Drawing Sheets

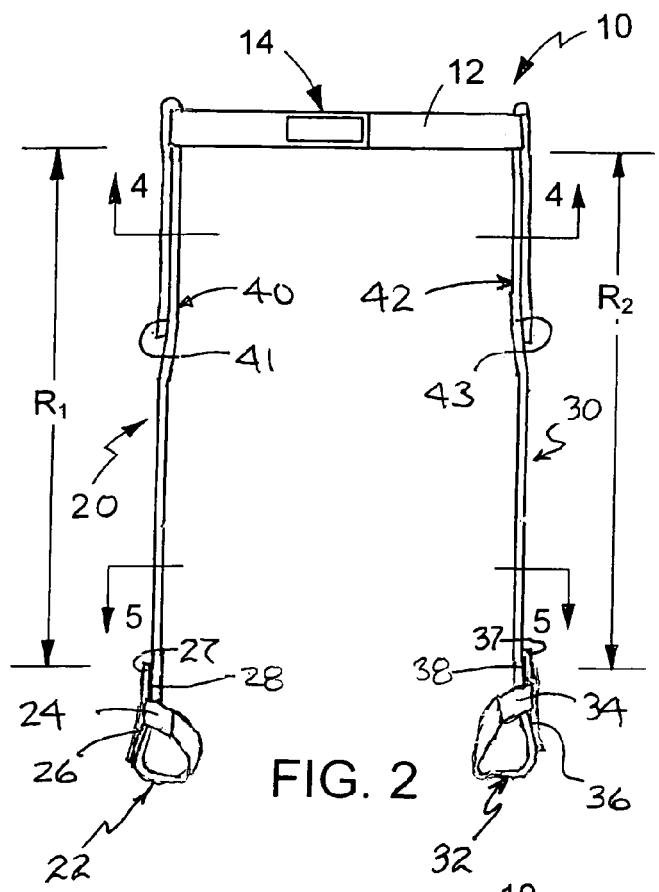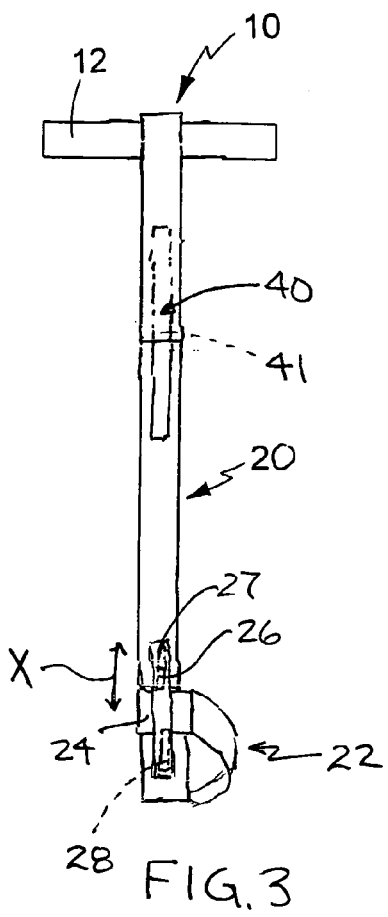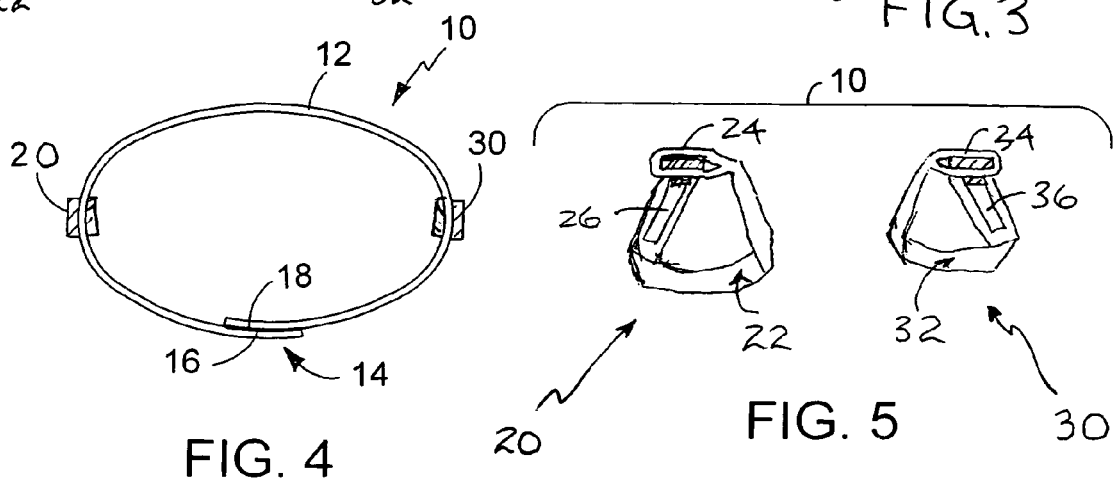
FIG. 2
FIG. 3
FIG. 4
FIG. 5

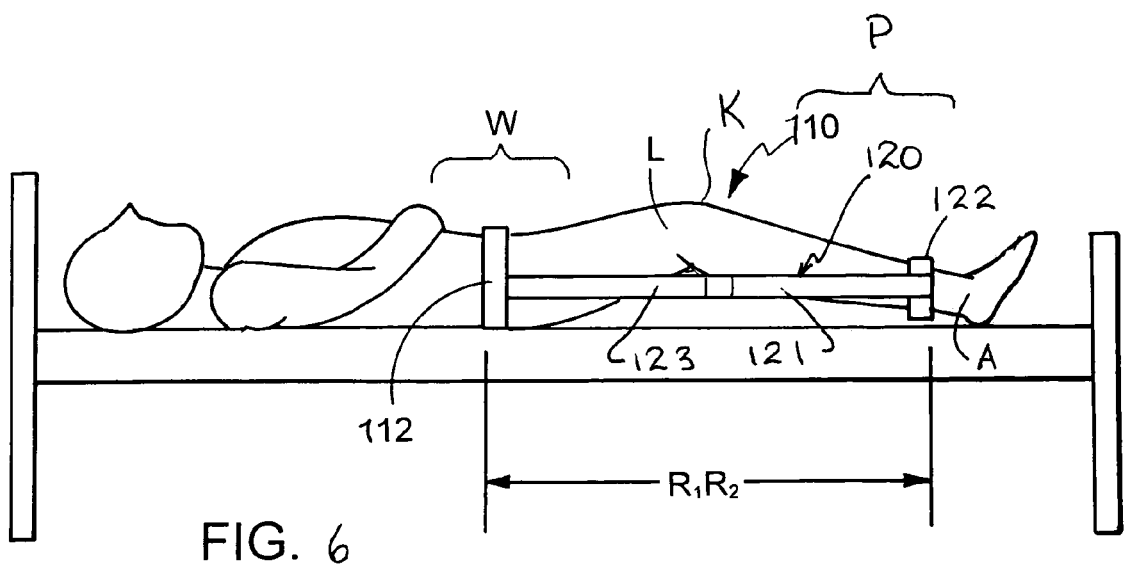
FIG. 6
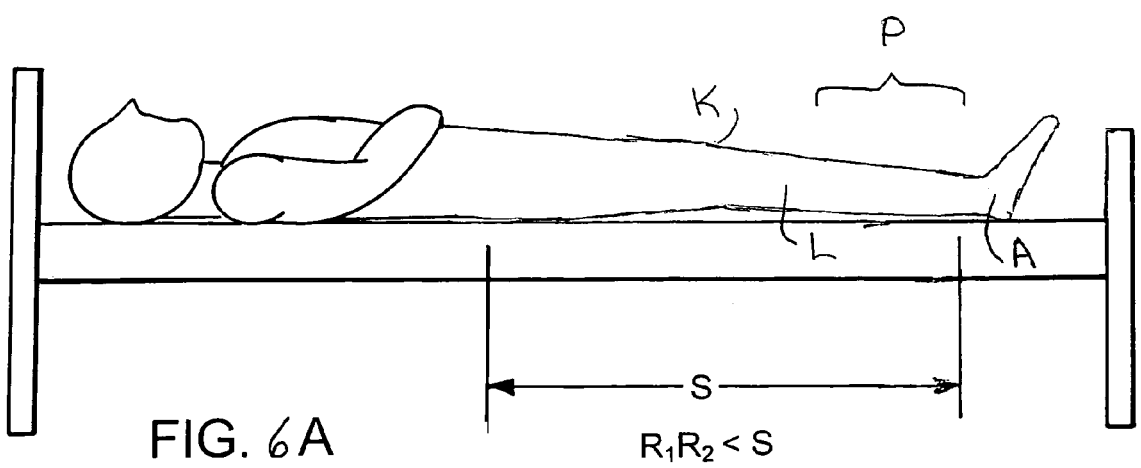
FIG. 6A    $R_1R_2 < S$

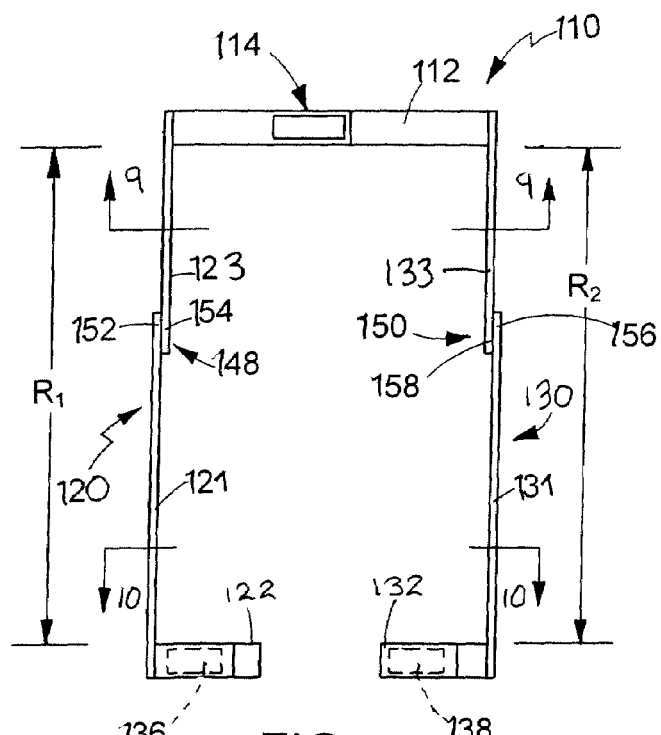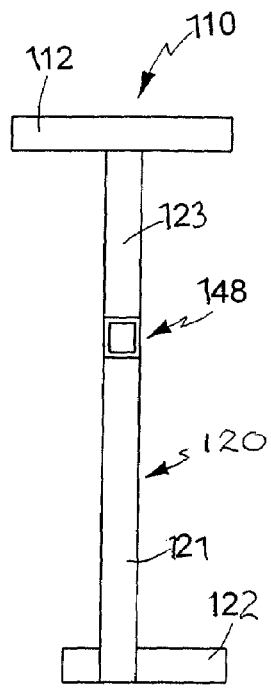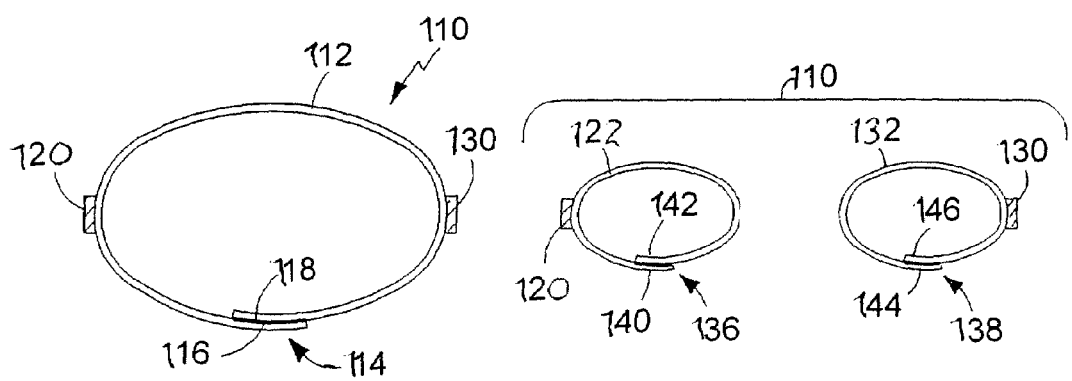

SLEEP-AIDING DEVICE

TECHNICAL FIELD

This application claims benefit from U.S. Provisional Patent Application No. 60/455,484, filed Mar. 18, 2003.

The invention relates to devices for aiding sleep, and more particularly to devices for reducing leg muscle cramping during sleep.

BACKGROUND

Many people find their sleep disturbed by muscle cramps, particularly of the legs.

SUMMARY

According to the invention, a sleep-aiding device for reducing leg muscle cramping during sleep comprises a belt member worn at a wearer's waist in use during sleep; a first leg member worn in use during sleep, with an upper end portion attached at the belt member and a lower end portion attached at a lower portion of a wearer's first leg, below the wearer's knee; and a second leg member worn in use during sleep, with an upper end portion attached at the belt member and a lower end portion attached at a lower portion of a wearer's second leg, below the wearer's knee. The leg members are adjustable to predetermined length between attachment at the belt member and attachment at the lower portions of the wearer's first legs, the predetermined lengths of the leg members being selected to restrict stretching of the wearer's legs to full extension during sleep.

Preferred embodiments of the invention may include one or more of the following additional features. The upper end portions of the leg members are attached at the belt portion by upper loops formed over the belt member. The lower end portions of the leg members define lower loops for receiving each of the wearer's feet therethrough. The lower loop of the first leg member in use during sleep encircles the wearer's first foot, e.g. in a region adjacent the wearer's first ankle and the lower loop of the second leg member in use during sleep encircles the wearer's second foot, e.g. in a region adjacent the wearer's second ankle. The lower loop of the first leg member defines a circumference adjustable to engage snuggly about the wearer's first foot and the lower loop of the second leg member defines a circumference adjustable to engage snuggly about the wearer's second foot. Preferably, the lower end portion of the first leg member terminates in a bottom end loop engaged about the first leg member for sliding positioning therealong for adjustment of the circumference of the lower loop of the first leg member, and the lower end portion of the second leg member terminates in a bottom end loop engaged about the second leg member for sliding positioning therealong for adjustment of the circumference of the lower loop of the second leg member. More preferably, the sleep-aiding device further comprises a first fastener for releasable securement of the bottom end loop of the first leg member along the first leg member and a second fastener for releasable securement of the bottom end lower loop of the second leg member along the second leg member. Preferably, the first fastener and the second fastener each comprises cooperative elements of hook-and-loop-type fasteners. Preferably, the sleep-aiding device further comprises cantilevered tabs disposed adjacent one or more of the hook-and-loop-type fasteners for facilitating adjustment. The belt member encircles the wearer's waist in use during sleep. Preferably, the belt member has an effective length adjustable to accommodate attachment about wearers of different waist dimensions. More preferably, the belt member defines a first end portion and an opposite second end portion and comprises a belt releasable fastener for adjustably joining the belt's first end portion and second end portion. The belt releasable fastener comprises cooperative hook-and-loop type fastener elements for varying the effective length of the belt member. Each of the first leg member and the second leg member comprises a releasable fasteners for adjustment of the predetermined length of each of the first leg member and the second leg member. Each releasable fastener comprises cooperative hook-and-loop type fastener elements for varying the predetermined length. The first leg member comprises a first strap member having an upper end attached to the belt member and an opposite lower end attached to a lower end portion, the lower end portion terminating in a first loop attached in use during sleep to a wearer's first leg, below the wearer's knee; and the second leg member comprises a second strap portion having an upper end attached to the belt member and an opposite lower end attached to a lower end portion, the lower end portion terminating in a second loop attached in use during sleep to a wearer's second leg, below the wearer's knee. Preferably, each of the first loop and the second loop encircles the wearer's associated lower leg in use during sleep. Each of the first leg member and the second leg member comprises a releasable fastener for attachment of the first loop and the second loop about each of the wearer's lower legs. Each of the first loop and the second loop is adjustable to accommodate attachment to wearers of different lower leg dimensions. Each of the releasable fasteners comprises cooperative hook-and-loop type fastener elements.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a somewhat diagrammatic side view of a person reclining in a bed, e.g., as during sleep, and equipped with one embodiment of a sleep-aiding device of the invention to restrict extension of the person's legs to a length, $R_1$, $R_2$; while

FIG. 2 is a front view of the sleep-aiding device of FIG. 1.

FIG. 3 is a side view of the sleeping aiding device of FIG. 2.

FIG. 4 is a bottom plan view of the sleep-aiding device of taken at the line 4-4 of FIG. 2.

FIG. 5 is a top plan view of the sleep-aiding device taken at the line 5-5 of FIG. 2.

FIG. 6 is a somewhat diagrammatic side view of a person reclining in a bed, e.g., as during sleep, and equipped with another embodiment of a sleep-aiding device of the invention to restrict extension of the person's legs to a length, $R_1$, $R_2$; while FIG. 6A is a similar view with the a person's legs fully extended to a length, S, greater than $R_1$, $R_2$.

FIG. 7 is a front view of the sleep-aiding device of FIG. 6.

FIG. 8 is a side view of the sleeping aiding device of FIG. 7.

FIG. 9 is a bottom plan view of the sleep-aiding device of taken at the line 9-9 of FIG. 7.

FIG. 10 is a top plan view of the sleep-aiding device taken at the line 10-10 of FIG. 7.

Like reference symbols in the various drawings indicate like elements.

DETAILED DESCRIPTION

Figure 1:
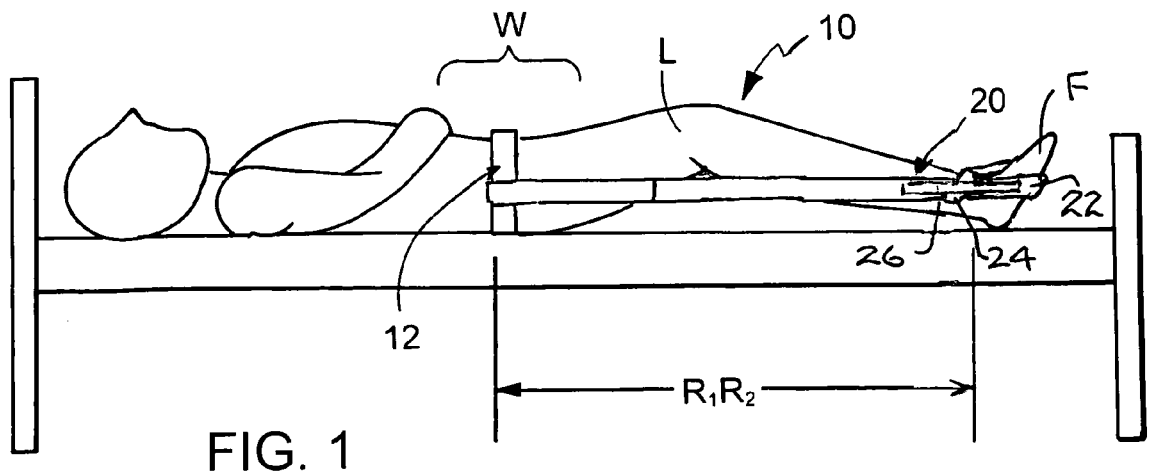

Referring to FIGS. 1-5, in one embodiment, a sleep-aiding device 20 for reducing leg muscle cramping during sleep includes a belt member 12 worn encircling the waist area, W, of a wearer during sleep. The belt has a releasable fastener 14, e.g. cooperative hook-and-loop type fastener elements 16, 18, for varying the effective length of the belt, thereby to permit adjustable attachment of the belt 12 about the wearer's waist, e.g. to accommodate attachment about wearers of different waist dimensions.

The sleep-aiding device further includes a first leg member 20 worn during sleep with the wearer's first foot, F, engaged in its lower loop 22, and a second leg member 30 worn during sleep with the wearer's second foot, engaged in it lower loop 32. In preferred embodiments, each of the first leg member 20 and the second leg member 30 terminates in a bottom end loop 24, 34 engaged about its respective leg member 20, 30 by sliding positioning therealong (arrow, X; FIG. 3) for adjustment of the circumferences of the lower loops 22, 32, e.g. to accommodate snug engagement about the wearer's feet, F, of different sizes. The positions of the bottom end loops 24, 34 along the respective leg members 20, 30 are adjustably secured by overlaying fastener strips 26, 36, each of which is fixedly secured, e.g. by stitching, at an upper end 27, 37 to the respective leg member 20, 30 and relatively fastened along their lengths, including above and below the positions of the bottom end loops 24, 34, by cooperative elements of hook-and-loop type fasteners 28, 38.

Figure 1A:
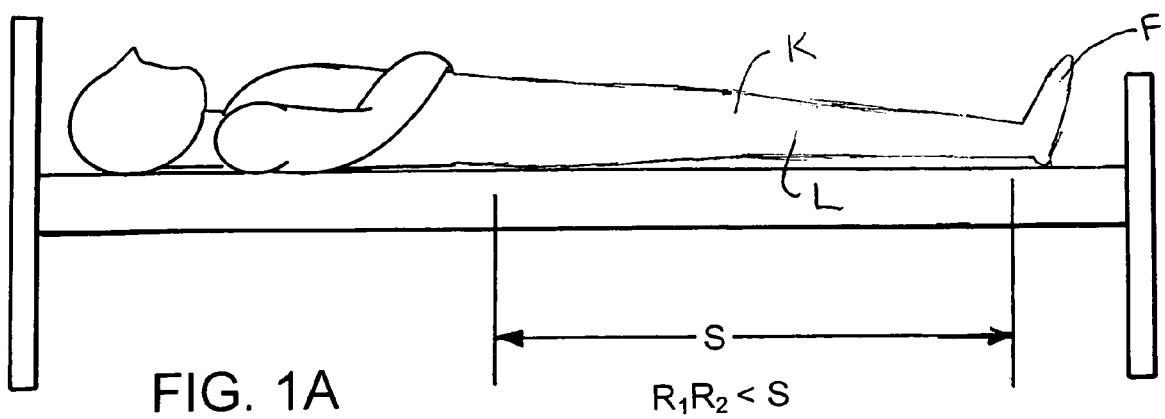
FIG. 1A is a similar view with the person's legs fully extended to a length, S, greater than $R_1$, $R_2$.

The first leg member 20 is attached in its upper region to the belt member 12. The second leg member 30 is also attached in its upper region to the belt member 12. In preferred embodiments, each of the leg members 20, 30 is looped over the belt member 12 and fastened upon itself by releasable fasteners 40, 42, e.g. cooperative hook-and-loop type fasteners 41, 43, respectively, for adjustment of the length, R, of the leg members 20, 30 below the belt member 12, e.g. to accommodate use by wearers having different leg lengths, S, when the legs, L, are stretched to full extension. The first leg member 20 is adjusted to a predetermined length, $R_1$, between attachment to the belt member 12 and attachment of the lower loop 22 about the wearer's first foot, F. The second leg member 30 has a predetermined length, $R_2$, between attachment to the belt member 12 and attachment of the lower loop 32 about the wearer's second foot, F. Each predetermined length, $R_1$, $R_2$, is selected to restrict stretching of the wearer's associated leg, L, to its length of full extension, S, during sleep. In particular, the predetermined length, R, of the leg members 20, 30 between attachment to the belt member 12 and attachment of the lower loops 22, 32 about each of the associated wearer's feet, F, is relatively less than a distance, S, between the same points at the wearer's waist and feet when the wearer's leg is stretched to full extension (FIG. 1A).

Referring next to FIGS. 6-10, in another embodiment, a sleep-aiding device 110 for reducing leg muscle cramping during sleep includes a belt member 112 worn encircling the waist area, W, of a wearer during sleep. The belt has a releasable fastener 114, e.g. cooperative hook-and-loop type fastener elements 116, 118, for varying the effective length of the belt, thereby to permit adjustable attachment of the belt 112 about the wearer's waist, e.g. to accommodate attachment about wearers of different waist dimensions.

The sleep-aiding device also includes a first leg member 120, consisting of a first lower portion 121 and a first (upper) strap member 123, and a second leg member 130, consisting of a second lower portion 131 and a second (upper) strap member 133. The first lower portion 121 terminates in a transverse loop 122 worn during sleep attached about a lower region, P, of a wearer's first leg, generally below the wearer's knee, e.g. in the region of the ankle. The second lower portion 131 terminates in a transverse loop 132 worn during sleep attached at a lower region, P, of a wearer's second leg, generally below the wearer's knee, e.g. in the region of the ankle. The transverse loops 122, 132 encircle the wearer's respective lower legs (ankles) during sleep, each of the transverse loops having a releasable fastener 136, 138, respectively, e.g. cooperative hook-and-loop type fastener elements 140, 142 and 144, 146, respectively, for adjustable attachment of the transverse loops 122, 132 about the wearer's lower leg (ankle), e.g. to accommodate attachment about wearers' legs of different dimensions. The first strap member 123 is attached at its upper end to the belt member 112, e.g. by stitching, and attached at its opposite lower end to the lower portion 121. The second strap member 133 is attached at its upper end to the belt member 112, e.g. by stitching, and attached at its opposite lower end to the lower portion 131. Preferably, the first leg member 120 has a predetermined length, $R_1$, between attachment to the belt member 112 and attachment at the lower region, P, of a wearer's first leg, e.g. about the region of the ankle. The second leg member 122 similarly has a predetermined length, $R_2$, between attachment to the belt member 112 and attachment at the lower region, P, of the wearer's leg, e.g. about the region of the ankle. Each predetermined length, $R_1$, $R_2$, is selected to restrict stretching of the wearer's associated leg, L, to its length, S, of full extension during sleep (FIG. 6A). In particular, the predetermined length, R, of the leg members 120, 130 between attachment to the belt member 112 and attachment at the lower regions, P, of the associated legs of the wearer (FIG. 6) is relatively less than a distance, S, between the same points at the wearer's waist and lower legs when the wearer's leg is stretched to full extension (FIG. 6A). Preferably, in this embodiment, each of the strap members 123, 133 has a releasable fastener 148, 150 respectively, e.g. cooperative hook-and-loop type fastener elements 152, 154 and 156, 158, respectively, for adjustment of the effective lengths, R, of the first and second leg members 120, 130, e.g. to accommodate use by wearers of different leg lengths, S, when stretched to full extension.

A number of embodiments of the invention have been described. Nevertheless, it will be understood that various modifications may be made without departing from the spirit and scope of the invention. For example, the belt fastener may have the form of a buckle with cooperative strap and eyelets or a tie. The leg members may have the form of ankle harnesses, spats, socks or similar. The strap members may be adjustably fastened by buckles or ties. The straps may be adjustably fastened at the belt and/or at the leg members. The straps may incorporate a limited degree of elasticity or stretch. Accordingly, other embodiments are within the scope of the following claims.

What is claimed is:

1. A sleep-aiding device for reducing leg muscle cramping during sleep comprising:

a belt member being worn at a wearer's waist in use during sleep;

a first leg member adapted to be worn in use during sleep, with an upper end portion attached at said belt member and a lower end portion attached at a lower portion of a wearer's first leg, said first leg member comprising a first strap member having an upper end attached to the belt member and an opposite lower end attached to a lower end portion, said lower end portion terminating in a first loop attached in use during sleep to a wearer's first leg, below the wearer's knee, at or above the wearer's ankle; and a second leg member being worn in use during sleep, with an upper end portion attached at said belt member and a lower end portion attached at a lower portion of a wearer's second leg, said second leg member comprising a second strap portion having an upper end attached to the belt member and an opposite lower end attached to a lower end portion, said lower end portion terminating in a second loop attached in use during sleep to a wearer's second leg, below the wearer's knee, at or above the wearer's ankle;

said first leg member being adjustable to a predetermined length between attachment at said belt member and attachment at the lower portion of the wearer's first leg and said second leg member being adjustable to a predetermined length between attachment at said belt member and attachment at the lower portion of the wearer's second leg, said predetermined length of said first leg member and said predetermined length of said second leg member being selected to restrict stretching of the wearer's legs to full extension during sleep.

2. The sleep-aiding device of claim 1, wherein each of said first loop and said second loop encircles the wearer's associated lower leg in use during sleep, below the wearer's knee, at or above the wearer's ankle.

3. The sleep-aiding device of claim 1, wherein each of said first leg member and said second leg member comprises a releasable fastener for attachment of said first loop and said second loop about each of the wearer's lower legs, below the wearer's knee, at or above the wearer's ankle.

4. The sleep-aiding device of claim 3, wherein each of said first loop and said second loop is adjustable to accommodate attachment to wearers of different lower leg dimensions, below the wearer's knee, at or above the wearer's ankle.

5. The sleep-aiding device of claim 3, wherein each of said releasable fasteners comprises cooperative hook-and-loop type fastener elements.

\* \* \* \* \*